(12) United States Patent
Griffin

(10) Patent No.: US 10,478,356 B2
(45) Date of Patent: Nov. 19, 2019

(54) SOFT, LIGHT-WEIGHT MALE URINE RECEPTACLE AND METHOD OF USE

(71) Applicant: Lorine B. Griffin, Evans, GA (US)

(72) Inventor: Lorine B. Griffin, Evans, GA (US)

( * ) Notice: Subject to any disclaimer, the term of this patent is extended or adjusted under 35 U.S.C. 154(b) by 442 days.

(21) Appl. No.: 15/235,901

(22) Filed: Aug. 12, 2016

(65) Prior Publication Data

US 2017/0042748 A1 Feb. 16, 2017

Related U.S. Application Data

(60) Provisional application No. 62/282,835, filed on Aug. 12, 2015.

(51) Int. Cl.
| | |
|---|---|
| A61F 13/56 | (2006.01) |
| A61F 13/47 | (2006.01) |
| A61F 13/471 | (2006.01) |
| A61F 13/64 | (2006.01) |
| A61F 13/15 | (2006.01) |

(52) U.S. Cl.
CPC ........ *A61F 13/5605* (2013.01); *A61F 13/471* (2013.01); *A61F 13/4704* (2013.01); *A61F 13/64* (2013.01); *A61F 2013/15146* (2013.01)

(58) Field of Classification Search
None
See application file for complete search history.

(56) References Cited

U.S. PATENT DOCUMENTS

| | | | |
|---|---|---|---|
| 4,601,716 A | 7/1986 | Smith | |
| 5,065,459 A | 11/1991 | Tjahaja et al. | |
| 5,695,485 A | 12/1997 | Duperret et al. | |
| 5,735,837 A | 4/1998 | Ishikawa | |
| 5,797,890 A | 8/1998 | Goulter et al. | |
| 5,827,250 A * | 10/1998 | Fujioka | A61F 5/4401 604/349 |
| 6,059,762 A | 5/2000 | Boyer et al. | |
| 6,113,582 A | 9/2000 | Dwork | |
| 6,119,280 A | 9/2000 | Rentsch | |
| 6,416,500 B1 * | 7/2002 | Wada | A61F 13/4704 604/346 |
| 6,479,726 B1 | 11/2002 | Cole | |
| 7,160,277 B2 | 1/2007 | Elson et al. | |
| 7,985,210 B2 | 7/2011 | Ashton et al. | |

(Continued)

*Primary Examiner* — Tatyana Zalukaeva
*Assistant Examiner* — Gabriella E Burnette
(74) *Attorney, Agent, or Firm* — Laurence A. Greenberg; Werner H. Stemer; Ralph E. Locher

(57) ABSTRACT

A male urine receptacle is provided that includes a liquid permeable inner layer, a liquid impermeable outer layer and an absorbent core located therebetween. The inner layer, outer layer and absorbent core are assembled together to form a layered assembly, which, when folded into a into a "U" configuration, defines a front portion and a back portion of the receptacle. At least a portion of the side edges between the front portion and the back portion are closed by sealing or otherwise securing together the side edges of the layered assembly. At least one of the closed sides forms an expandable gusset and, preferably, both sides include at least one gusset. A closure mechanism is configured to adjust the open, upper periphery of the receptacle to provide a comfortable fit onto a penis, thus retaining the male urine receptacle on the penis.

15 Claims, 4 Drawing Sheets

(56) References Cited

U.S. PATENT DOCUMENTS

| | | | |
|---|---|---|---|
| 8,187,238 B1* | 5/2012 | Dupree | A61F 5/451 |
| | | | 604/347 |
| 8,277,426 B2 | 10/2012 | Wilcox et al. | |
| 8,500,708 B2* | 8/2013 | Glenn | A61G 9/006 |
| | | | 4/144.1 |
| 8,696,641 B1 | 4/2014 | Williams, III | |
| D704,330 S | 5/2014 | Cicatelli | |
| 9,370,411 B2 | 6/2016 | Guardia | |
| 2002/0193762 A1* | 12/2002 | Suydam | A61F 5/4556 |
| | | | 604/327 |
| 2009/0216209 A1 | 8/2009 | Ekstrom | |
| 2015/0000027 A1* | 1/2015 | Hughes | A47K 11/00 |
| | | | 4/479 |
| 2015/0250656 A1* | 9/2015 | Maksimow | A61F 5/453 |
| | | | 604/374 |

* cited by examiner

SOFT, LIGHT-WEIGHT MALE URINE RECEPTACLE AND METHOD OF USE

CROSS-REFERENCE TO RELATED APPLICATIONS

The present application claims benefit of Provisional Patent Application No. 62/282,835, filed on Aug. 12, 2015; that application being incorporated herein, by reference, in its entirety.

BACKGROUND OF THE INVENTION

Field of the Invention

The present invention relates to disposable absorbent urinals, and more particularly to a disposable absorbent male urine receptacle, designed primarily for users with little or no mobility.

Description of the Related Art

In certain unfortunate circumstances, an individual may lack the mobility to relieve himself utilizing standard restroom facilities and toilets. These events may occur when the individual is elderly, bedridden either in a hospital or at home, too weak to walk and may be confined to a wheelchair, etc., If such events occur when the individual is being hospitalized, a catheter may typically be inserted into the individual. While suitable for their intended purpose, catheters are very uncomfortable for the patient, provide an avenue for infections, and also limit the mobility of the individual even if the user is able to utilize a wheelchair, or the individual may be given the hand held plastic urinal. For some individuals based on their condition, the hand held plastic urinal can be uncomfortable, bulky, hard to handle, and the possible chance for spills.

Male urinals designed to be worn or affixed to the patient are known. For example, U.S. Pat. No. 8,696,641, issued on Apr. 15, 2014 to Williams, Ill., discloses a male incontinence containment device having a sleeve made of flexible mesh that firmly grips the penis along the entire shaft of the penis. The '641 patent discloses gripping action on the penis is similar to a "Chinese Handcuff" which may be somewhat irritating to a user especially as the gripping action is along the entire length of the penis.

U.S. Pat. No. 8,277,426, issued on Oct. 2, 2012 to Wilcox discloses a male urinary incontinence device having a hammock-like effect. The '426 patent discloses a shell attached to the body forming a cavity adapted to hold the male genitalia, which can be uncomfortable to the genitalia and the glue may irritate the skin.

U.S. Pat. No. 6,119,280, issued on Sep. 19, 2000 to Rentsch discloses an all plastic leak-proof urinal having a bottle neck, a flat disk-like cap, handle and lid. An all plastic urinal, as disclosed in the '280 patent, can be uncomfortable to a user. It can also be an embarrassment to the patient having a bottle of urine hanging from the bed. Further, if the plastic urinal drops spillage may occur.

There is a need for a male urine receptacle that is designed primarily for users with little or no mobility, which is comfortable and which is sufficient for containing the urine in a manner which is not painful or unpleasant for the user.

There is further needed a male urine receptacle that provides a custom fit, applies no pressure to the penis shaft, has no drainage tubing and no leakage, will not automatically tighten around the penis shaft and is not glued to any part of the body. There is s further need for a urinal that is soft, light weight and disposable, which is comfortable for the penis head, which is very easy to use by the user or caregiver and which is easily disposed of.

Additionally, there is a need for a more reliable male urine receptacle primarily designed for users with little or no mobility. The male urine receptacle is comfortable and sufficient for containing the urine in a manner which is not unpleasant for the user or caregiver. Other advantages of one or more aspects will be apparent from consideration of the drawings and ensuring description.

BRIEF SUMMARY OF THE INVENTION

The present invention is particularly suited to overcome those problems which remain in the art in a manner not previously known or contemplated. In accordance with one embodiment, a more reliable, disposable, male urine receptacle is provided primarily for users with little or no mobility. In one particular embodiment, the male urine receptacle is made from soft materials including a liquid permeable inner layer, a liquid impermeable outer layer and a highly absorbent core suitable for absorbing urine. In one embodiment, the layers surround the core and the resultant device produced forms an offset "U" shaped configuration, inside the receptacle, for positioning against a male penis. In a further particular embodiment, the absorbent core is sized to retain approximately 8 to 16 ounces (240 cc-480 cc) of urine.

Additionally, in one embodiment of the invention, a male urinal is provided that is soft, flexible and light-weight, and which includes an enclosure mechanism with a stretchable portion and a securing tab, to enable the upper periphery of the receptacle to provide a constrictive force for retaining the urine receptacle onto the users penis.

Although the invention is illustrated and described herein as embodied in a soft, light-weight mail urine receptacle and method of use, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings. However, it should be understood that the present device is not limited in its application to the details of construction and arrangements of the components set forth in the description or drawings, as there may be other various executions and embodiments not described that are in keeping with the scope and spirit of the present invention.

BRIEF DESCRIPTION OF THE DRAWINGS

The foregoing background, as well as the following detailed description of the preferred embodiments, is better understood when read in conjunction with the appended drawings. For the purpose of illustrating the invention, there is shown in the drawings an exemplary embodiment that is presently preferred, it being understood however, that the invention is not limited to the specific methods and instrumentality's disclosed. Additionally, like reference numerals represent like items throughout the drawings. In the drawings.

DETAILED DESCRIPTION OF THE INVENTION

Before explaining the disclosed embodiment of the present invention in detail, it is to be understood that the invention is not limited in its application only to the details of the particular arrangement shown since the invention is capable of other embodiments. Also, the terminology used herein is for the purpose of description and not of limitation. For purposes of the present application, the terms "urine receptacle", "male urine receptacle", "male urinal", "urine receptacle", "soft male urine receptacle", "urine cup" and "soft urine cup" will be used interchangeably herein.

Figure 3:
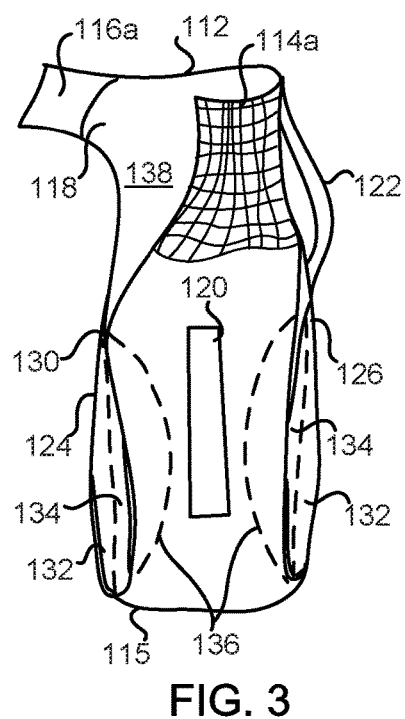
FIG. 3 is a further perspective view from the front of an open soft urine cup illustrating folded gussets in accordance with one particular embodiment of the invention.
Figure 4:
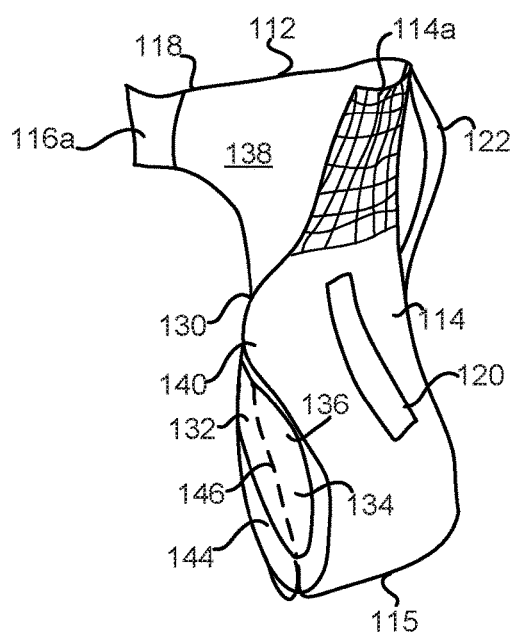
FIG. 4 is a further perspective view from the front of an open soft urine cup illustrating a gusset and anti-leak channel in accordance with one particular embodiment of the invention.
Figure 5:
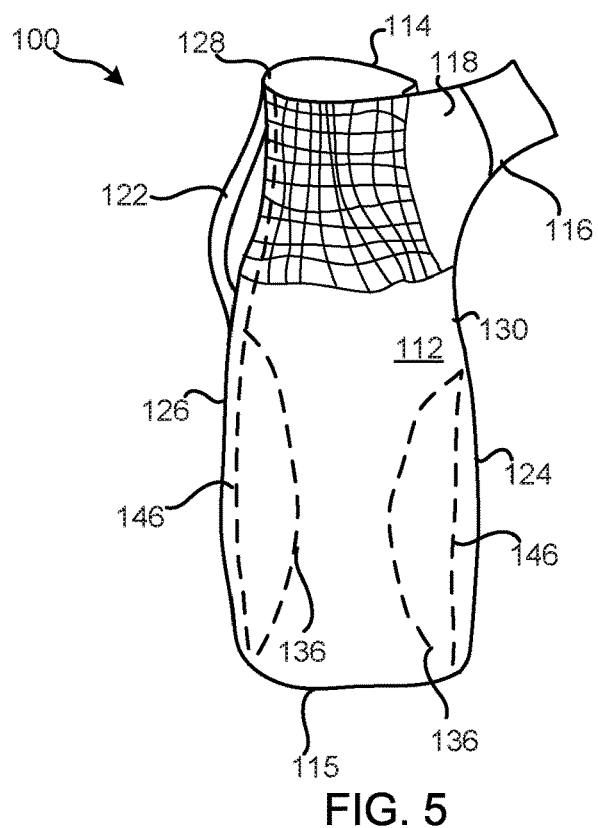
FIG. 5 is a perspective view from the back of an open soft urine receptacle in accordance with one particular embodiment of the invention.

Referring now to FIGS. 1-5, there is illustrated a male urine receptacle or urine cup 100, in accordance with one particular embodiment of the invention. In the present embodiment, the male urine receptacle 100 is soft, flexible, light-weight and, most preferably, disposable. The urine receptacle 100 has a body 111 including a back portion 112 and a front portion 114. The back portion 112 of the body 111 is constructed with a fairly non-stretchable fabric for providing stability. However, preferably, at least the upper part 114a of the front portion 114 of the body 111 includes a sturdy, stretchable fabric having elastomeric materials integrated within the fabric, so as to allow the fabric to stretch to a certain width, while exhibiting restrictive force, for providing a secure fit circumferentially around a penis 110. If desired, at least some of the back portion 112 can additionally be made from a sturdy stretchable fabric, as illustrated in FIG. 5. The back portion 112 and the front portion 114 of the urine receptacle 100 are sized and configured for encircling a shaft and head of the penis 110.

A closure strap 116 extends from the back portion 112 and is provided to secure the soft urine receptacle 100 securely (but not too tightly), around the shaft of the penis 110. In one embodiment, the closure strap 116 includes a first stretchable extension member 118 and a refastenable securing tab 116a. The refastenable securing tab 116a may be constructed from a number of different suitable materials, such as elastomeric materials, standard adhesive made of polypropylene, magic tape or mechanical tape, such as a hook and loop fastener such as VELCRO™. The first stretchable extension member 118 may be constructed from a number of different suitable materials, including, but not limited to, non-woven materials, breathable or non-breathable film and/or spun-bond polypropylene fiber. In one particular embodiment, the extension member 118 is not stretchable, but rather, is made from soft, rigid, elastomeric materials with a fairly non-stretchable portion, while the remaining part of the top portion of the body 111 is stretchable.

In one particular preferred embodiment of the invention, the soft male urine receptacle is worn by a user wearing ordinary (unmodified) underwear or briefs. In this case, if desired, the male urine receptacle can be attached to the underwear of the user and held in place using a fastener strip 120, which may be an adhesive strip or a hook type mechanical fastener strip, as desired. In one particular embodiment of the invention, the strip 120 is an 8 cm×2 cm (3 inch×¾ inch) adhesive strip mounted on the front of the body 111 of the soft urine 100, just below the stretchable front portion 114, for use when the urine receptacle 100 is worn inside the underwear of a user. In another particular embodiment, a soft handle 122 is attached to the upper portion of the body 111 of the urine receptacle 100, between the back portion 112 and the front portion 114, at the seam just below the mid-point, to help a user having a short penis shaft support and adjust the urine receptacle 100.

Figure 1:
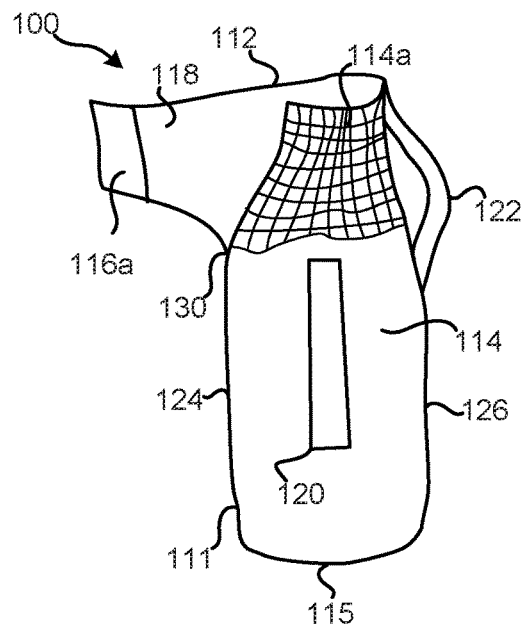
FIG. 1 is a perspective view from the front of an open soft urine cup in accordance with one particular embodiment of the invention.
Figure 2:
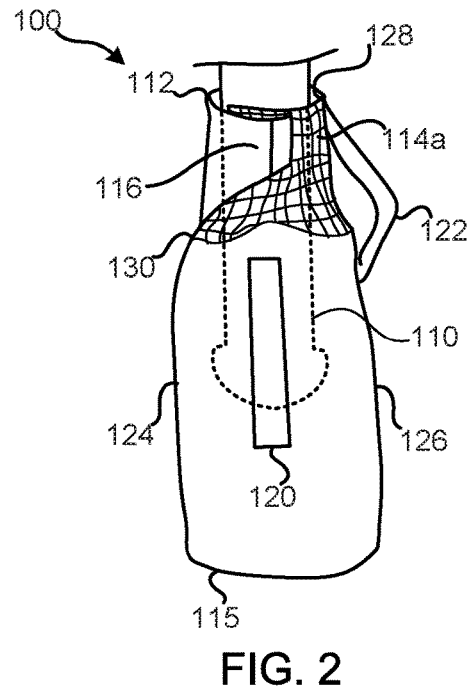
FIG. 2 is a perspective view from the front of a closed soft urine cup inserted in accordance with one particular embodiment of the invention having a penis.

As illustrated more particularly in FIG. 2, the first stretchable extension member 118 may be pulled just tight enough to offset the refastenable securing tab 116a to the upper part 114a of the front portion 114, thereby establishing a mouth 128 for receiving the penis 110 into the urine cup 100. In one preferred embodiment, the urine cup 100 has a rectilinear profile defined by the back and front portions 112, 114. The urine cup 100 is closed at the left and right sides 124, 126 and at the bottom 115, so as to form a cup having an interior accessible via the mouth 128, through which the penis shaft and head are received. In one particular embodiment of the invention, the urine cup 100 has a total length of between 7.5 to 9 inches. Additionally, in another embodiment, when folded at the mid-point 130, the urine cup 100 is 5 to 5.5 inches long and 3 to 3.5 inches wide.

In one particular embodiment, the urine cup 100 is manufactured from multiple layers that are integrated to provide a single body 111. Preferably, the urine cup 100 is manufactured from a composite web structure which lies flat in an unfolded configuration. In one preferred embodiment, the body 111 is folded about itself at a midpoint 130 binging the respective ends opposite one another. In other words, the single body 111 is basically formed into a "U" shape. Once the penis shaft and head are properly positioned between the back portion 112 and the front portion 114, the stretchable extension 118 can be stretched to overlay the upper part 114a of the front portion 114 and the refastenable securing tab 116a can be attached to the front portion 114, so as to close the mouth 128 around the shaft and head of the penis 110, so as to secure the urine cup 100 in place.

Referring more particularly to FIGS. 3-5, testing of a soft male urine receptacle according to the present invention has shown that the inclusion of gussets 136 on the sides 124, 126 (near the bottom 115 of the urine cup 100) is critical to the correct operation of the urine receptacle 100, because they permit expansion of the receptacle 100. The gussets 136 are formed at the edges 124, 126 of the urine cup 100. In one particular preferred embodiment illustrated, there are four gusset halves, two (132, 134) on the left side 124 and two (132, 134) on the right side 126, starting from just below the mid-point 130 and extending to near the bottom 115 of the urine cup 100. In this embodiment, each right gusset half 132 is carried by, or part of, the back portion 112, while each gusset half 134 is carried by, or part of, the front portion 114. In operation, the gusset halves 132, 134 can be created when the right and left sides 124, 126 of the body 111 are folded. After folding, the respective gusset halves 132, 134 are seamed together to create the full gusset 136, which extends into the body 111, towards the interior of the urine cup 100. In one particular embodiment of the invention, the body 111 has a mid-point 130, such that when the body 111 is folded the back portion 112 and the front portion 114 are generally offset from one another.

In one preferred embodiment of the invention, the gusset halves 132, 134 are glued, welded, sewn or otherwise engaged with an outer edge of the inner layer 138 of the body 111, and extend between a mid-point 130 and the bottom 115. This is not meant to be limiting, however, as the gussets 136 may be formed by a number of different methods known in the art without departing from the scope and spirit of the present invention. One method involves securing a separately constructed gusset 136 to the top surface of the outer layer 140 or otherwise engaged with, an outer edge of the inner layer 138 using glue, heat welding, sonic welding, sewing, etc. An optional anti-leak channel 144 may be glued or otherwise engaged with the constructed gusset 136 for an abundance of caution. The anti-leak channel or band 144 is a stretchable barrier that is designed to help prevent leakage by channeling and holding a heavy flow of urine, until the urine can be absorbed into the absorbent core 142. The anti-leak channel 144 may be constructed from a number of different suitable materials, such as polyurethane or polyester, synthetic rubber (for example, spandex), hydrophilic non-woven materials that allow the urine to flow into the core 142, etc. The anti-leak channel 144 may additionally be made from an elastic material or include elastic fibers, to permit the channel to additionally stretch to hold the excess urine until it can be absorbed. The above-described construction enables the body 111 to expand to accommodate the accumulated urine. Devices not having one or more gussets 136 were found not to perform satisfactorily and leakages were incurred.

Referring more particularly to FIGS. 3-6, the urine cup 100 provides a male urine receptacle with components previously described in connection with FIGS. 1-5. In one particularly preferred embodiment of the invention, the urine cup 100 features a layered assembly, which includes a web structure with a fluid-permeable inner layer 138, a liquid impermeable, but vapor-permeable, polyethylene outer layer 140, and an absorbent core 142. In one particular embodiment, the absorbent core is selected to retain 8 to 16 ounces (240 cc-480 cc) of urine. Urine output can be measured by weight prior to application to obtain a dry weight and post weight after utilization.

The inner layer 138 is the part of the urine cup 100 that comes in contact with the penis skin. The inner layer 138 may be constructed from a wide range of suitable materials including non-woven webs of natural fibers (e.g., wood or cotton) or synthetic fibers (e.g., polypropylene or polyester), a combination of such webs or fibers, or aperture film. One suitable inner layer material may be 15 gsm spunbond polypropylene from Avgol Non-woven Fabrics of Holon, Israel. In addition, the inner layer 138 may be treated with a surfactant to facilitate liquid transfer, especially at a central zone of the inner layer 138 over the absorbent core 142 and an inner surface of the inner layer 138 may be treated with a chemical to increase the surface tension of liquid passing through the material.

For purposes of the description, the term "inner layer" 138, as used herein, may refer to any sheet, layer or composite that covers at least the absorbent core 142, but preferably extends beyond the absorbent core 142 toward the longitudinal side edges 124, 126 of the receptacle 100. Further, the term "inner layer," 138, as used herein, may refer to any assembly, unitary or integrally, of sheets, layers, or composites applied at least over the absorbent core 142, and any part, portion, region or section thereof.

For purposes of description, the term "outer layer" 140 as used herein, may refer to any sheet, layer or composite that covers at least the absorbent core 142, but preferably extends laterally beyond the absorbent core 142 toward the side edges of the body 111. Further, the term "outer layer," 140 as used herein, may refer to any assembly, unitary or integrally, of sheets, layers, or composites applied at least over the absorbent core 142 and any part, portion, region or section thereof.

The outer layer 140 is the waterproof outer shell and may be constructed from a number of different suitable materials and, preferably, will have a breathable or vapor-permeable attribute (distinguishing it from liquid-permeable) so that air can pass there through. In one embodiment, the outer layer 140 is constructed from a polyolefin film. Alternatively, the outer layer 140 may be formed from a combination of a liquid-permeable, non-woven material and a film barrier that is laminated on the non-woven material. The film barrier may or may not be vapor-permeable, as desired. Further, the film barrier may be applied as a mask in a central area of the web structure that has an overall width less than the width of the other outer layer 140 materials but covers the absorbent core 142. One suitable construction for the outer layer 140, includes an outer layer of spun bond polypropylene fiber with a basis weight of about 15 gsm (grams/square meter) available from BBA Non-wovens, of Simpsonville, S.C. and (available from BBA Non-wovens, of Simpsonville, S.C.) and a polyethylene film of about 0.5 mil (0.0005") thickness adhesively laminated to the outer layer. Such a polyethylene film is available from, and manufactured by, Exxon Chemical USA, of Houston, Tex. The film may be laminated using adhesive available from National Starch & Chemical Company of Bridgewater, N.J. Yet another suitable construction for the outer layer 140 includes a web of spun bond or SMS (spunbond, backslash, meltblown, backslash, spunbond) non-woven material and breathable or non-breathable films of 0.5 mils to 2.0 mils in thickness.

Sandwiched between the inner layer 138 and outer layer 142 is the absorbent core 142, which absorbs fluids released inside the urine cup 100. The absorbent core 142 is generally elongated and rectangular. The absorbent core 142 is generally centered about the longitudinal axis and lateral axis of the receptacle 100, and firmly secured between the inner layer 138 and outer layer 140. The absorbent core 142 is preferably made of an absorbent composition adapted to absorb bodily liquids received through the inner layer 138.

In one preferred embodiment, the absorbent composition includes a fluffed wood pulp component for wicking and structural integrity and a high absorbency material (or super absorbent) for containing liquids. The absorbent core 142 can additionally be made from a super absorbent gelling material, if desired. However, this is not meant to be limiting, as the receptacle, according to the present invention, is equally adapted to utilize absorbent cores of varying shapes and compositions, as well as other types of cores known in the art.

The gussets 136 and the anti-leak channel 144, may be constructed from a number of different suitable materials, such as polyurethane or polyester, synthetic rubber (spandex), hydrophilic non-woven which allows the urine to flow into the core and a hydrophobic non-woven design to prevent leakage.

Figure 6:
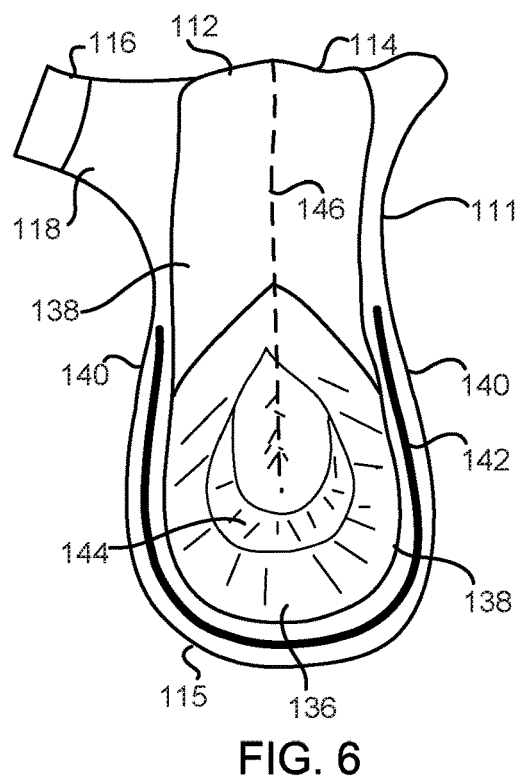
FIG. 6 is a partial, cut-away view of a urine receptacle in accordance with one particular embodiment of the invention.
Figure 7:
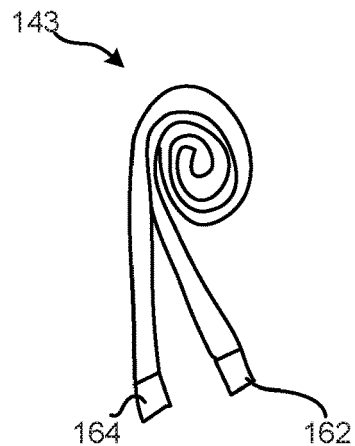
FIG. 7 is a perspective view of a rolled up waistband or belt that can be used with the urine receptacle in accordance with one particular embodiment of the invention.
Figure 8:
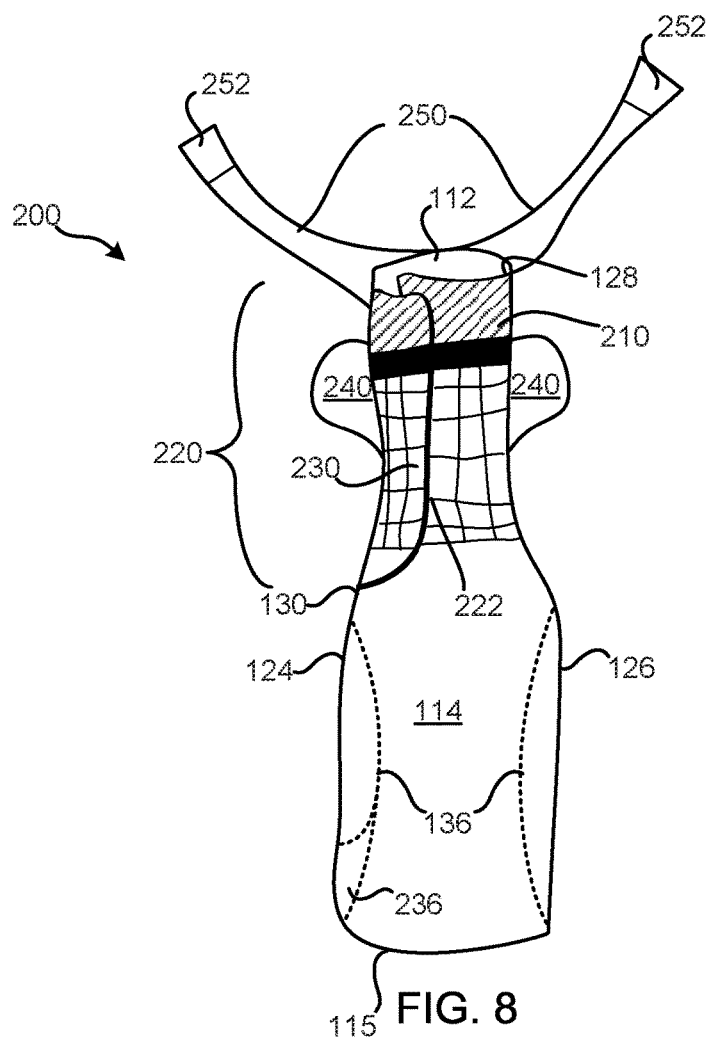
FIG. 8 is a perspective view from the front of an soft urine cup with the ears and braces open, in accordance with another embodiment of the invention.
Figure 9:
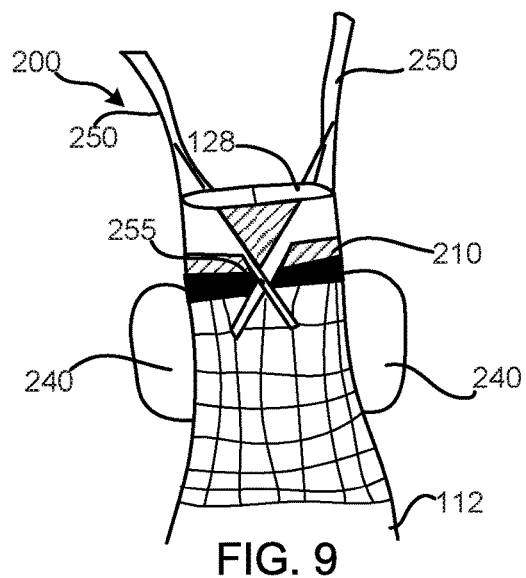
FIG. 9 is a partial view from the back of the top portion of a urine cup according to FIG. 8 having the ears and braces open.
Figure 10:
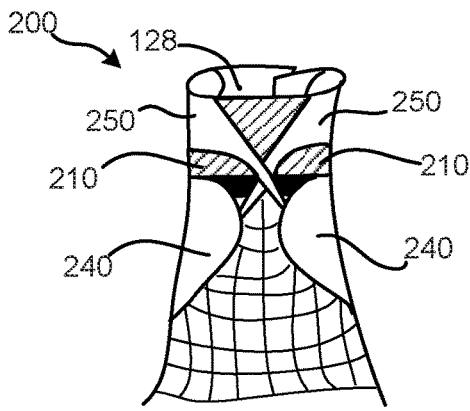
FIG. 10 is a partial view from the back of a soft urine cup according to one embodiment of the invention wherein the ears and braces are closed.
Figure 11:
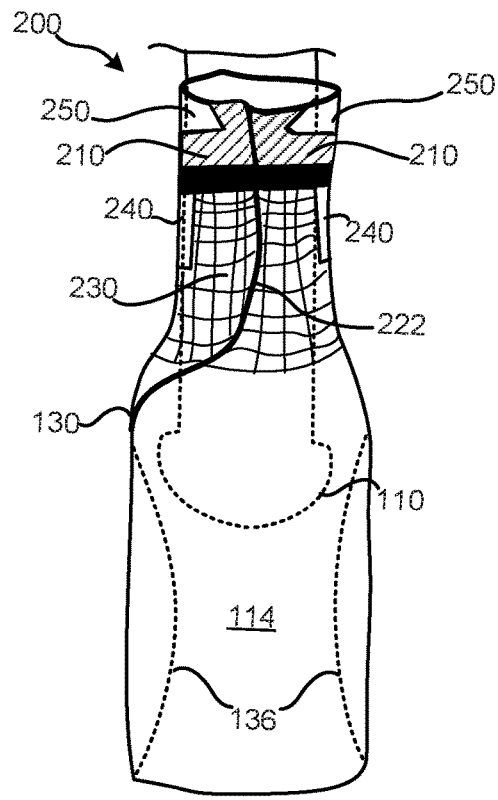
FIG. 11 is a perspective view, taken from the front of the soft urine cup of FIG. 8 with the ears and braces closed.

As illustrated more particularly in FIG. 6, the single body 111 of the urine cup 100 is folded to form a "U" shape and sealed at the edges 124, 126, in order to form the urinal or cup. In this configuration the side opposite from the refastenable securing tab 116 is attached along the entire length of the respective side establishing a seam 146 with the gusset 136 folded inward toward the interior of the urine cup 100. In this way, the seam 146 is disposed internally enabling portions of the respective back portion 112 and front portion 114 to overhang the seam 146. By being disposed internally, portions of the edge of the respective sides can be folded internally and secured along the internal folded portion. This overhang provides for the flexibility of the gusset 136 to extend. Seam 146 preferably extends to the top of the urine cup 100 on the closed side 126, connecting the top and bottom portions of the unfolded body together. In this manner, the top and bottom portions of the unfolded body 111, when folded together form a mouth 128 into the interior of the urine cup 100.

On the opposite side of the full seam 146, the edge 124 is closed or seamed to the midpoint 130, thus leaving parts of the back portion 112 and front portion 114 separable from one another. This enables the urine receptacle 100 to have a mouth 128 that may be expanded for receiving the penis head and shaft of the user. Once the receptacle 100 is properly positioned around the penis head and shaft, the first stretchable extension member 118 and the refastenable securing tab 116 is constructed to overlay and attach to the part 114a, creating a closed mouth 128 around the shaft and head of the penis 110, thus securing the urine cup 100 in place.

Referring now to FIGS. 8-11, there will be described a soft, light-weight, disposable urine cup 200 in accordance with another embodiment of the present invention. More particularly, the urine cup 200 is like the urine cup 100 in many respects, including, but not limited to, its size, capacity, construction materials and arrangement. For example, in one preferred embodiment, the urine cup 200 has a body formed in an elongated rectangular shape. Additionally, the urine cup 200 is constructed to include an inner layer, outer layer and absorbent core exactly as described in connection with the urine cup 100 herein above. However, in addition to the like elements (denoted in the figures by like reference numbers), the urine cup 200 further includes a soft, sturdy collar 210 that accepts the tip or head of the penis 110. In one particular embodiment of the invention, the back and front portions of the collar 210 extend between 1 to 2 inches in height. The collar 210 is attached to the urine cup 200 at the topmost portion of the tunnel 220 created when the urine cup 200 is closed. In one particular embodiment of the invention, the collar 210 is constructed from of a sturdy soft stretchable fabric having elastomeric materials integrated within the fabric, enabling the fabric to stretch to a certain width while exhibiting restrictive force for providing a secure fit.

The tunnel 220 forms the neck of the urine cup 200 and, in one preferred embodiment, has a split 222 on one side to allow the diameter of the tunnel 220 to be adjusted. In one particular embodiment of the invention, the diameter has an adjustable diameter from 2 to 3 inches and is 2.5-3.5 inches in length. In one particular embodiment, the split 222 is selected to be 2.5 to 3 inches in length. In one embodiment, the split 222 extends from the top of the collar 210 to the bottom of the tunnel 220, just above the midpoint 130.

The split 222 allows the tunnel 220 to open up and allow the penis 110 access through the collar 210. The tunnel 220 can be constructed as a single sheet with no seam or, if desired, can be a part of the back and front portions 112, 114. The tunnel 220 portion of the urine cup 200 can be made from a hydrophobic or moisture resistant material, if desired, so that urine will flow down the tunnel into the pocket or bowl of the urine cup 200, where it wicks through the inner layer wall to an absorbent core, as described above in connection with core 142. Alternatively, the bowl portion of the urine cup 200 can include a super absorbent gelling material therein, which absorbs the urine leakage and keeps moisture away from the skin of the user. One advantage to making the tunnel 220 portion of the urine cup 200 from a moisture resistant material, is that, even when the urine cup 200 is spoiled, the collar 210 and walls of the tunnel 220 remain dry.

Figure 12:
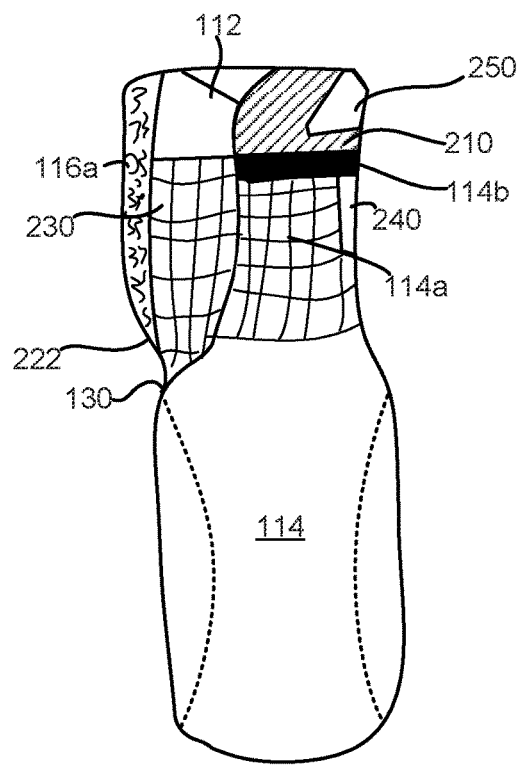
FIG. 12 is a perspective view, taken from the front of the soft urine cup of FIG. 8 with the closure strap open, but the ears and braces closed.

In one embodiment of the invention, the width of the back portion of the urine cup 200 is extended about 1 to 1.5 inches longer, than the width of the front portion, to provide a closure strap 230 that overlaps and overlays the upper part 114a of the front portion 114 of the urine cup 200, in use, and can be used to secure the tunnel closed after the urine cup 200 is soiled. The closure strap 230 extends from the top edge of the collar 210 to just above the midpoint 130 and operates similarly to the closure strap 116 described in connection with FIGS. 1-7 and is preferably. As illustrated more particularly in FIG. 12, the outer edge of the back portion of the closure strap 230 includes a securing strip 116a that is preferably ½ inch to 1 inch in width and can be an adhesive and/or mechanical fastener, as described above. In one particular embodiment, the closure securing strip 116a is a hook or loop fastener that mates with a corresponding hook or loop fastener 114b on the upper part 114a. The closure strap 230 can be secured to a front portion of the tunnel 220. When not in use the closure strap 230 is pressed against the outside wall of the tunnel 220.

Preferably, each of the collar 210, tunnel 220 and closure strap 230 are constructed of a sturdy stretchable fabric having elastomeric materials integrated within the fabric enabling the fabric to stretch to a certain width while exhibiting restrictive force for providing for a secure fit.

In one particular preferred embodiment of the invention, the portion of the urine cup 200 forming the tunnel 220 is either made from a water resistant/waterproof material, or is saturated with a waterproof coating, while the remainder of the urine cup 200 is formed as described above. Thus, in use, urine will flow down the waterproof tunnel 220, past the midpoint 130, and will pass through the liquid permeable inner layer and be absorbed into a super absorbent gelling material or other absorbent core located between the inner and outer layers.

In particular, the pocket or bowl portion (extending from the midpoint 130 to the bottom 115) is designed to receive urine leakage and wick the urine to an absorbent core between an inner layer and an outer layer of the urine cup 200, as described above in connection with the urine cup 100. For example, the liquid permeable inner layer may be constructed from a wide range of suitable materials such as non-woven webs of natural fibers, plastic-treated material, synthetic fibers, breathable film etc. The outer layer may be waterproof and constructed from a wide range of suitable materials, such as, a breathable material that permits air to pass through, polyolefin film, etc. The absorbent core may be made from any suitable material such as a high absorbency material, fluffed wood pulp, synthetic polymer, microfiber materials, a super absorbent gelling material, etc. The urine cup 200 can be adapted to utilize absorbent cores of varying shapes and compositions, as well as other types of cores, as desired.

Referring back to FIGS. 8-12, in the particular embodiment of the invention illustrated, the urine cup 200 is additionally provided with a pair of ears 240 attached to the upper left and right sides of the collar 210. Ears 240 can be used to help the user or caregiver adjust the position of the urine cup 200, i.e., giving the user or caregiver a portion of the tunnel that can be grasped while the urine cup 200 is being placed on the user. When not in use, the ears 240 are pressed against the back of the tunnel 220.

Additionally, the urine cup 200 is designed to include right and left full gussets 136, which have been found to be critical to the optimal absorption of urine leaked into the urine cup 200, to accommodate expansion and/or overflow. Such gussets 136 can be formed, as described above in connection with the urine cup 100. For example, the left sides 124 of the back portion 112 and front portion 114 can be seamed (or glued) together starting at the bottom of the gusset and ending just above the mid-point 130, below the tunnel 220, while the right sides 126 can be seamed or glued together from the bottom of the gusset 136 to the top of the collar 210, if desired. The gussets 136 can be constructed of materials such as polyurethane, polyester foam, etc., Additionally, if desired, a crescent shaped gusset 236 may be seamed or glued to the inside bottom of the right and/or left gussets 136.

Figure 13:
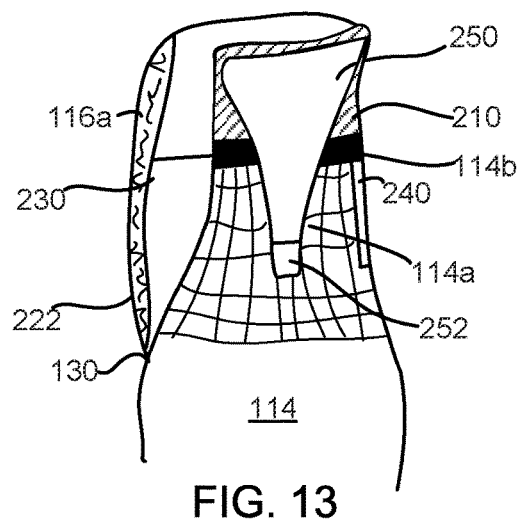
FIG. 13 is a partial perspective view of a soft urine cup in accordance with a further embodiment of the invention.

Referring back to FIGS. 8-11, the urine cup 200 additionally includes, in the present embodiment, a pair of elasticized braces 250 attached to the collar 210. More particularly, the braces 250 may be seamed, glued or otherwise secured to the right and left sides of the collar 210. In one particular embodiment, the braces 250 are joined in an x-shape 255 on the back of the collar 210, to eliminate bunching of the straps. The braces 250 can be adjusted, i.e., raised or lowered, so that the penis 110 is comfortably situated. Additionally, if desired, the braces 250 can be affixed to a waistband (143 of FIG. 7) by means of a soft, suitable, tearaway adhesive, such as adhesive pads 162, 164 on the belt or 252 on the braces 250. When not in use, the braces can be pressed down within the wall of the tunnel. In an alternate embodiment illustrated in FIG. 13, a single brace 250, and not a pair of braces 250, if desired.

Operation—Method of Use:

Referring now to FIGS. 1-12, the manner of using the urine cup 100, 200 according to the present invention, to accommodate the accumulated urine is not identical to the method used for existing male urinals. To use the urinal 100 of the present invention, one will open the mouth 128 of the urinal by taking the folded first stretchable extension member 118 and refastenable securing tab 116*a* from the interior top portion of the Urine cup 100, creating a mouth 128 for the penis 110. Similarly, to use the urinal 200, the closure strap 230 can be removed from a portion of the tunnel 220 to form a mouth 128. Next, one will position the penis 110 through the mouth 128 and inside the chamber formed between the back portion 112 and the front portion 114. With the urine cup 200, the ears 240 can be grasped and used to assist with the positioning. Subsequently, one pulls the stretchable extension member 118 or closure strap 230 across to the front portion 114 and secures it to the upper part 114*a* of the front portion 114. The refastenable securing tab or strip 116*a* will adhere to the upper part 114*a* to provide a custom fit retaining the urine cup 100, 200 onto the penis 110.

Next, if the stretchable waistband 143 and/or the fastener strip 120 are to be used (out of an abundance of caution), one will attached the stretchable waistband 143 by exposing the adhesive tips 162, 164 and placing them at any point on the urine cup 100 that is suitable for the user or, with the urine cup 200, on the braces 250. Similarly, if the fastener strip 120 is to be used, the urine cup 100, 200 is first positioned on the penis 110 and then secured to the underwear brief at a point that is suitable for the user.

To remove the urine cup 100, 200, if the stretchable waistband 143 and fastener strip 120 are in use, one will release the stretchable waistband 143 by pulling back the adhesive tips 162, 164 or 252 releasing the urinal 100, 200. Next, the fastener strip 120 is released from the underwear brief by pulling one of the urine cup 100, 200 or underwear brief away from the other one of the urine cup 100, 200 or underwear brief, to release the hold of the strip 120 on the underwear brief. The urinal 100, 200 can then be unsecured from the penis 110 by releasing the refastenable securing tab 116*a* from the upper part 114*a* to remove the stretchable extension member 118 and open the mouth 128 of the urine cup 100, 200, thus releasing the penis 110. To dispose of the removed urine cup 100, 200, refastenable securing tab 116*a* is wrapped tightly around the mouth of the soiled urine cup 100, 200, to offset the first stretchable extension member 118 thereby establishing a closed urinal 100, 200.

It can be seen from the foregoing that the urine cup 100, 200 described herein is designed primarily for users with little or no mobility, and provides a urinal that is more reliable and much needed. The urine cup 100, 200 of the present invention utilizes a single body having a soft mouth to accept the penis 110 with no pressure to the penis shaft. It is light-weight and completely disposable. The closure strap 116 or closure strap 230 adheres to the upper portion 114*a*, or to a closure strip 114*b*, of the urinal 100, 200, providing a custom fit for retaining the penis 110.

For quick and easy removal of the urine cup 100, 200, tear away the closure strap 116 or closure strap 230, thus, releasing the penis 110. Note that, it is not always necessary to fasten the urinal onto the penis; the urinal is just as reliable if the user is only going to urinate in the urine cup and not leave it on. For example, a long distance truck driver or someone stuck in a snow storm for hours. The urine cup will not automatically tighten around the penis shaft, urine output can be measured by weight measurement, no lid or end cap, no closure strings, no soiled pad to replace, not attached to the groin area with glue and has no leg straps.

As can be seen, the urine cup of the present invention provides a urinal having a custom fit, applies no pressure to the penis shaft, has no drainage tubing and no leakage, will not automatically tighten around the penis shaft and is not glued to any part of the body. The device of the present invention is not a drip collector, male diaper or pad, male urinary catheter or hard plastic urinal; it is not intended to be a wearable garment designed for active men who engage freely in normal daily activities. This urinal is a soft, light weight disposable urine cup which is comfortable for the penis head, very easy to use by the user or caregiver and easily disposed of. The urine cup according to the above-described embodiments has the additional advantages in that:

- It allows the core to be made of different materials, such as super absorbent polymers (SAP), synthetic polymer, hydrophilic polymer and wood pulp;
- It allows the core to have microfiber materials;
- It allows the core to be of different sizes, such as small, medium and large; It allows the core to be of different shape such as square, oval, rectangle and isosceles triangle;
- The absorbent core will retain 8 to 16 ounces (240 cc-480 cc) of urine in a variety of sizes without requiring the manufacturer to use a separate facility for assembling together the inner layer and outer layer enclosing the absorbent cores;
- Readily available, inexpensive materials, such as polypropylene, elastomeric material, dry fibrous material, standard adhesive, etc., may be used;
- It allows the inner layer to be constructed from polypropylene, and may enhanced with aloe and vitamin E;
- The outer layer may be constructed from petroleum-based plastic, plastic-treated material, polyethylene film and bioplastic;
- The device can be made perfume free and with a wetness indicator, if desired;
- It provides an offset spacing between the front and back portion providing a side access for receiving a penis into the interior of the receptacle, this side access may be on the right side, the left side, the front and the back of the urinal;
- It provides a soft handle for the shorter penis shaft, the handle may be long or short, on the right or lift site of the device;
- An adjustable, elastic waist belt with tear-away adhesive tabs, having different sizes and widths may, optionally, be provided, although some users may choose not to use the belt;
- Other materials may be used for the gusset such as, polyurethane, polyester foam, etc;
- The gussets are specially designed to expand and retain urine, while a leak guard may, optionally, be seamed or glued near the bottom of each gusset for maximum gusset leak protection;
- One or two gusset(s) of various shape and size may be seamed or glued to the right and left side of the cup which enables the body to expand and prevent leakage;
- Hot melts may be used to glue the different components of the gussets and/or the urine cup; and
- Specialty glue may be used for integrity, to help reduce breaking apart of the layers when wet.

Additionally, the urine receptacle of the present invention advantageously provides a male urinal that is not hard and bulky with lids and caps; is not attached to the body with glue; does not have a gripping action similar to a Chinese Handcuff along the entire length of the penis; does not have an elastic band that grips the skin at the base of the penis; that can be used for minor urinary leakage or dribbling; which is not an adult diaper or male catheter.

While the invention has been described, disclosed, illustrated and shown in various terms of certain embodiments or modifications, which it has presumed in practice, the scope of the invention is not intended to be, nor should it be deemed to be, limited thereby and such other modifications or embodiments as may be suggested by the teachings herein are particularly reserved, especially as they fall within the breadth and scope of the claims here appended. For example, the gussets can be constructed with more than one piece, have other shapes, such as oval, square, rectangular, etc. Accordingly, while a preferred embodiment of the present invention is shown and described herein, it will be understood that the invention may be embodied otherwise than as herein specifically illustrated or described, and that within the embodiments certain changes in the detail and construction, as well as the arrangement of the parts, may be made without departing from the principles of the present invention as defined by the appended claims.

DRAWING REFERENCE NUMBERS 100 urine receptacle or cup;
110 penis;
111 urine receptacle body;
112 back portion;
114 front portion;
114a upper part of the front portion;
114b closure strip;
115 bottom of the urine cup;
116 closure strap;
116a refastenable securing tab;
118 first stretchable extension member;
120 fastener strip;
122 soft handle;
124 left side;
126 right side;
128 mouth;
130 midpoint;
132 right gusset half;
134 left gusset half;
136 full gusset;
138 inner layer;
140 outer layer;
142 absorbent core;
143 stretchable waistband;
144 anti-leak channel;
146 seam;
162 adhesive tip;
164 adhesive tip;
200 soft urine cup;
210 collar;
220 tunnel;
222 split;
230 closure strap;
236 crescent gusset;
240 ear;
250 brace;
252 fastener; and
255 x-shape.

I claim:

1. A disposable male urine receptacle, comprising: a liquid impermeable outer layer; a liquid permeable inner layer; an absorbent core suitable for absorbing urine disposed between said liquid permeable inner layer and said liquid impermeable outer layer; said inner layer, said outer layer and said absorbent core being assembled together to form a layered assembly and folded into a body having a "U" configuration including a front portion and a back portion; at least one expandable gusset formed between said front portion and said back portion; wherein at least one expandable gusset is formed by two edges of the layered assembly being joined together and folded inward between the front and back portion at each left and right side of the body; closure mechanism overlaying an upper portion of the body of said urine receptacle, said closure mechanism including a closure strap affixed to one of said back portion or said front portion and extendable across said side of the body to said other one of said back portion or said front portion, said closure strap configured to releasably attach to said other one of said back portion or said front portion to permit a size adjustment to be made to said upper portion to provide a constrictive force onto a penis of a user in order to retain the urine receptacle on the penis.

2. The urine receptacle of claim 1, wherein the two edges of the layered assembly are secured together at a seam by glue.

3. The urine receptacle of claim 1, wherein the urine receptacle is rectilinear in shape.

4. The urine receptacle of claim 1 wherein said front portion and said back portion are joined along the entire length of one side of the receptacle, and a second side opposite said one side is closed partially along the length of the urine receptacle, said closure mechanism extending from said partially closed second side.

5. The urine receptacle of claim 4, wherein said closure strap includes a fastener tab for fastening the closure strap to the other one of the back portion and the front portion of the receptacle.

6. The urine receptacle of claim 1 wherein, the upper portion of said body includes soft, stretchable materials and a remaining portion of said body is fairly non-stretchable.

7. The urine receptacle of claim 6, wherein the upper portion of the body forms a tunnel including at least a portion of said closure mechanism.

8. The urine receptacle of claim 7, wherein said tunnel is waterproof.

9. The urine receptacle of claim 1, wherein the upper portion of said body is banded by a soft collar and at least one brace is attached to said collar.

10. The urine receptacle of claim 1 further including a handle element for holding the receptacle while positioning.

11. The urine receptacle of claim 10, wherein the handle includes a pair of ears.

12. A method of making a urine receptacle, comprising the steps of: providing a liquid impermeable layer, a liquid permeable layer and an absorbent core suitable for absorbing urine; layering the liquid impermeable layer and liquid permeable layer with the absorbent core therebetween to form a layered assembly; folding the layered assembly to form a body having a "U" configuration, with the liquid impermeable layer on the outside of the "U" configuration and the liquid permeable layer on the inside of the "U" configuration, the body including a front portion and a back portion; forming at least one expandable gusset between said front portion and said back portion; wherein at least one expandable gusset is formed by two edges of the layered assembly being joined together and folded inward between the front and back portion at each left and right side of the body; and forming a closure mechanism overlaying an upper portion of the body of said urine receptacle, said closure mechanism including a closure strap affixed to one of said back portion or said front portion and extendable across said side of the body to said other one of said back portion or said front portion, said closure strap configured to releasably attach to said other one of said back portion or said front portion, to permit a size adjustment to be made to said upper portion to provide a constrictive force onto a penis of a user in order to retain the urine receptacle on the penis.

13. The method of claim 12, wherein said closure mechanism configured to permit a size adjustment to be made to said upper portion to provide a constrictive force onto a penis of a user in order to retain the urine receptacle on the penis.

14. A method of using a male urine receptacle comprising;
providing a urine receptacle according to claim 1;
opening the closure mechanism to produce a partial separation at a side of said "U" shaped body;
inserting a penis through a mouth of said urine receptacle and into said "U" shaped configuration; and
closing said closure mechanism by affixing said closure strap to said other one of said back portion or said front portion, after inserting the penis, to provide a constrictive force on the penis with an upper periphery of the receptacle to retain the urine receptacle on the penis.

15. The method of claim 14, further comprising the step of using a positioning member on the receptacle to position the receptacle on the penis, wherein the handle is at least one of a handle and ears.

* * * * *